(12) United States Patent
Golz-Berner et al.

(10) Patent No.: US 7,906,158 B2
(45) Date of Patent: Mar. 15, 2011

(54) MOISTURE-REGULATING COSMETIC

(75) Inventors: Karin Golz-Berner, Monaco (MC); Leonhard Zastrow, Monaco (MC)

(73) Assignee: Coty Prestige Lancaster Group GmbH, Mainz (DE)

( * ) Notice: Subject to any disclaimer, the term of this patent is extended or adjusted under 35 U.S.C. 154(b) by 506 days.

(21) Appl. No.: 11/739,294

(22) Filed: Apr. 24, 2007

(65) Prior Publication Data
US 2007/0269400 A1 Nov. 22, 2007

(51) Int. Cl.
*A61K 36/889* (2006.01)
*A01N 65/00* (2009.01)
*A61K 36/00* (2006.01)

(52) U.S. Cl. ........ 424/727; 424/725; 424/774; 424/777; 424/70.1

(58) Field of Classification Search .......... None
See application file for complete search history.

(56) References Cited

U.S. PATENT DOCUMENTS

| 5,997,889 | A | * | 12/1999 | Durr et al. ............... 424/401 |
| 5,998,341 | A | * | 12/1999 | Bhandary et al. ......... 510/155 |
| 6,551,606 | B1 | * | 4/2003 | Golz-Berner et al. ....... 424/401 |

FOREIGN PATENT DOCUMENTS

| DE | 1617365 A1 | 4/1971 |
| DE | 19738303 A1 | 3/1999 |
| EP | 1185244 B | 9/2004 |

OTHER PUBLICATIONS

Palm_Oil.pdf.*
Palm_Oil_October_2009.pdf.*

* cited by examiner

Primary Examiner — Robert A Wax
Assistant Examiner — William Craigo
(74) Attorney, Agent, or Firm — Millen, White, Zelano & Branigan, P.C.

(57) ABSTRACT

The invention relates to a cosmetic composition with a moisture-regulating effect based on plant active ingredients with a long-lasting moisturizing effect of up to 24 hours. The cosmetic comprises in each case a watery plant milk of the fruit of *Elaeis guinensis*, of the leaves of *Phoenix canariensis*, of the rice husks of *Oryza sativa*, of the fruit of *Cocos nucifera*, and a honey complex consisting of acacia honey, eucalyptus honey, pine honey and lavender honey.

14 Claims, No Drawings

MOISTURE-REGULATING COSMETIC

The invention relates to a cosmetic composition with a moisture-regulating effect.

An enzyme-containing cosmetic with a regenerative effect for the skin is known from EP 1185244 and contains vegetable milk waters from bananas, dandelion, bindweed plants, poppy and/or soya together with a coconut milk concentrate and an alcoholic extract of honey/rice germ oil/rice husk oil. In addition to its cell-regenerating effect, a moisture-regulating effect is also described which lasts essentially for eight hours.

For dry skin, the emphasis in cosmetic compositions is mostly on the moisture-regulating effects, which means that there is a need to achieve not only stronger but also much longer-lasting moisturizing effects.

The object of the invention is to develop a cosmetic composition based on vegetable active ingredients that has a long-lasting moisturizing effect of up to 24 hours.

According to the invention, the cosmetic comprises
(a) a watery plant milk of a fruit of *Elaeis guinensis*,
(b) a watery plant milk of the leaves of *Phoenix canariensis*,
(c) a watery plant milk of rice husks of *Oryza sativa*,
(d) a watery plant milk of the fruit of *Cocos nucifera*,
(e) a honey complex consisting of acacia honey, eucalyptus honey, pine honey and lavender honey
as well as a residual share of up to 100 wt. % of cosmetic auxiliary substances, carrier substances and other active substances.

It has been found that the milk obtained by cold pressing the palm fruit of *Elaeis guinensis*, a West African palm, can cause an increase in the corneocyte volume and an improvement in the transepidermal water loss (TEWL) in interaction with the other ingredients. The share of palm fruit milk is in the range of 0.1 to 10 wt. % based on the total weight of the cosmetic and preferably in the range of 0.5 to 5 wt. %. Especially preferred are contents of 0.5 to 2.8 wt. %.

A further improvement in the moisturizing effect in interaction with the other ingredients of the cosmetic has been found with the watery palm leaf milk of *Phoenix canariensis*. The share of palm leaf milk is in the range of 0.1 to 5.0 wt. % based on the total weight of the cosmetic and preferably in the range of 0.6 to 2.0 wt. %.

Rice husk milk of *Oryza sativa*, which also contains phytosterols and proteins and has an antioxidant and moisturizing-reinforcing effect, is added in a share in the range of 0.1 to 5.0 wt. % based on the total weight of the cosmetic and preferably in the range of 0.5 to 2.5 wt. %.

To uphold the cell-regenerating effect, the already known watery plant milk of the fruit of *Cocos nucifera* is contained. This contributes to the degradation of fatty acid triglycerides by means of the enzymes contained therein. Their share is in the range of 0.1 to 7.0 wt. % based on the total weight of the cosmetic and preferably in the range of 0.2 to 3.0 wt. %.

Particularly advantageous for the long-lasting effect in moisture regulation is the use of a honey complex consisting of acacia honey, eucalyptus honey, pine honey and lavender honey, where the share of honey components can be in the respective ratios of 1:0.5-1.4:0.4-1.3:0.6-1.8, and the complex's share of the cosmetic is in the range of 0.1 to 5.0 wt. % based on the total weight of the cosmetic and preferably in the range of 0.1 to 2.5 wt. %.

In clinical studies it has been found that skin hydration with a single application and with a 100% increase over the initial value measured immediately afterwards only declines very slowly and shows a significant improvement at 35% above the initial value after 8 hours and still at 15-18% above the initial value after 24. The results of the study with continued daily application over a period of 4 weeks also show that the water content of the skin is on average around 40% higher than the initial values and declines only very slowly even when the daily treatment is discontinued.

The inventive cosmetic can be employed in certain cosmetic application forms. Such forms of application are, e.g. lotion, gel, day cream, night cream, sun cream, sun milk, after-sun products, spray, balm, mask, makeup, hand cream, body care product and/or hair product.

The corresponding application form contains not only the quoted active products, but also cosmetic auxiliary and carrier substances, as usually employed in such preparations, e.g. water, preservatives, colorants, pigments with a colouring effect, thickeners, fragrances, alcohols, polyols, esters, electrolytes, gelling agents, polar and non-polar oils, polymers, copolymers, emulsifiers, waxes and stabilizers.

Further additional active substances can also be employed in addition to the quoted active products. These additional active substances include, e.g. inorganic and organic light stabilizers, free-radical scavengers, moisturizing agents, vitamins, enzymes, further plant active substances, polymers, antioxidants, antiphlogistic natural active substances, oxygen-loaded asymmetrical lamellar aggregates according to WO 94/00109, decomposition products of yeasts or plant substances, produced by means of a gentle decomposition process using ultrasound according to WO 94/13783, kaolin, and kaolin modified with $SiO_2$ according to WO 94/17588.

The antioxidants include vitamins such as vitamin C and derivatives thereof, e.g. ascorbyl acetate, phosphate and palmitate; vitamin A and derivatives thereof; folic acid and its derivatives, vitamin E and its derivatives such as tocopheryl acetate; superoxide dismutase; flavones or flavonoids; amino acids such as histidine, glycine, tyrosine, tryptophan and derivatives thereof; carotenoids and carotenes, e.g. α-carotene, β-carotene; uric acid and derivatives thereof; α-hydroxy acids such as citric acid, lactic acid and malic acid.

It is also advantageous to add corresponding water- and/or oil-soluble UVA or UVB filters or both to the cosmetic compositions. The advantageous oil-soluble UVB filters include 4-aminobenzoic acid derivatives such as 4-dimethylaminobenzoic acid 2-ethylhexyl ester; esters of cinnamic acid such as 4-methoxycinnamic acid 2-ethylhexyl ester; benzophenone derivatives such as 2-hydroxy-4-methoxybenzophenone; 3-benzylidenecamphor derivatives such as 3-benzylidenecamphor.

Water-soluble UVB filters include, for instance, sulphonic acid derivatives of benzophenone or of 3-benzylidenecamphor or salts such as the Na or K salt of 3-phenylbenzimidazole-5-sulphonic acid.

The UVA filters include dibenzoylmethane derivatives such as 1-phenyl-4-(4'-isopropylphenyl)propane-1,3-dione, butylmethoxybenzoylmethanes and menthyl anthranilates.

Particularly preferred are benzophonone-3, butyl methoxydibenzoylmethane, octyl methoxycinnamate, octyl salicylate, 4-methylbenzylidene camphor, homosalate, octocrylene, ethylhexyl methoxycinnamate, isoamyl-p-methoxycinnamate, octyl dimethyl PABA, ethylhexyl triazone, diethylhexyl butamido triazone, ethylhexyl salicylate, methylene bis-benzotriazolyl tetramethylbutylphenol, disodium phenyl dibenzimidazole tetrasulphonate, bis-ethylhexyloxyphenol methoxyphenyl triazine.

Also usable as sun protection filters are inorganic pigments based on metal oxides, such as $TiO_2$, $SiO_2$, $ZnO$, $Fe_2O_3$, $ZrO_2$, $MnO$, $Al_2O_3$, which can also be used in a mixture.

Particularly preferred as inorganic pigments are agglomerated substrates of $TiO_2$ and/or ZnO, which have a content of spherical and porous $SiO_2$ particles, said $SiO_2$ particles having a particle size in the range of 0.05 μm to 1.5 μm, and, along with the $SiO_2$ particles, other inorganic particulate substances with a spherical structure, said spherical $SiO_2$ particles with the other inorganic substances forming defined agglomerates with a particle size in the range of 0.06 μm to 5 μm (according to WO 99/06012).

Another preferred active substance additive for the inventive cosmetic is a preparation with a high radical protection factor (see WO 99/66881) with a content of a product obtained by extraction of the bark of Quebracho blanco and subsequent enzymatic hydrolysis (Radicalys® from Greentech, France), and a non-ionic, cationic or anionic hydrogel or a mixture of hydrogels, and one or more phospholipids, and water. This preparation can be supplemented if necessary with a yeast decomposition product containing superoxide dismutase and/or cyclodextrins (WO 94/13783).

The oils used in the invention can be conventional cosmetic oils, such as mineral oil; hydrogenated polyisobutene, squalane produced synthetically or from natural products, cosmetic esters or ethers which can be branched or unbranched, saturated or unsaturated; vegetable oils, or mixtures of two or more thereof.

Especially suitable oils are, for example, silicone oils, mineral oils, hydrogenated polyisobutene, polyisoprene, squalanes, tridecyl trimellitate, trimethylpropane triisostearate, isodecyl citrate, neopentylglycol diheptanoate, PPG-15-stearyl ether as well as vegetable oils, such as calendula oil, jojoba oil, avocado oil, macadamia nut oil, castor oil, cocoa butter, coconut oil, maize oil, cottonseed oil, olive oil, palm nut oil, rapeseed oil, safflower oil, sesame oil, soyabean oil, sunflower oil, wheat germ oil, grapeseed oil, candlenut oil, thistle oil and mixtures thereof.

Depending on which oils are selected, the cosmetic properties of the solid composition are affected, such as degree of transparency, softness, hardness and spreading effect.

Suitable as esters or ethers are, for example, dipentaerythrityl hexacaprilate/hexacaprates/tridecyl trimellitate/tridecyl stearate/neopentyl glycol dicaprylate dicaprate, propylene glycol dioctanoate, propylene glycol dicaprylate 2,30 dicaprate, tridecyl stearates/neopentyl glycol dicaprylate dicaprate/tridecyl trimellitate, neopentyl glycol dioctanoate, isopropyl myristate, diisopropyl dimer dilinoleate, trimethylpropane triisostearate, myristyl ether, stearyl ether, cetearyl octanoate, butyl ether, dicaprylyl ether, PPG1-PEG9 lauroyl glycol ether, PPG15 stearyl ether, PPG14 butyl ether, Fomblin HC25.

As softening agents, a multitude of compounds can normally be employed, such as stearyl alcohol, glyceryl monoricinoleate, glyceryl monostearate, propane-1,2-diol, butane-1,3-diol, cetyl alcohol, isopropyl isostearate, stearic acid, isobutyl palmitate, isopropyl myristate, isopropyl palmitate, oleyl alcohol, isopropyl laurate, decyl oleate, octadecane-2-ol, isocetyl alcohol, cetyl palmitate, silicone oils such as dimethyl polysiloxane, polyethylene glycol, lanolin, cocoa butter, vegetable oils such as maize oil, cottonseed oil, olive oil, mineral oils, butyl myristate, palmitic acid etc.

Preferred as moisturizers are glycerol, butylene glycol, polypropylene glycol and mixtures thereof.

For emulsification, anionic, amphoteric, non-ionic or cationic surfactants or mixtures thereof can be used as surface-active agents.

The invention also relates to the use of a cosmetic for the long-lasting moisturizing of the skin, said cosmetic comprising a watery plant milk of the fruit of *Elaeis guinensis*, a watery plant milk of the leaves of *Phoenix canariensis*, a watery plant milk of the rice husks of *Oryza sativa*, a watery plant milk of the fruit of *Cocos nucifera* and a honey complex consisting of acacia honey, eucalyptus honey, pine honey and lavender honey.

The invention will be explained in greater detail below with reference to examples. All the details are given in weight percent unless otherwise stated.

EXAMPLE 1

Cream

| Phase A | |
|---|---|
| Water | q.s. ad 100 |
| Glycerol | 2.5 |
| Phase B | |
| Beheneth-25 | 3.0 |
| Cetearyl alcohol | 2.0 |
| Shea butter | 9.0 |
| Phase C | |
| Honey complex* | 1.0 |
| Palm fruit milk of *Elaeis guinensis* | 0.4 |
| Palm leaf milk of *Phoenix canariensis* | 0.6 |
| Rice husk milk of *Oryza sativa* | 0.5 |
| Palm fruit milk of *Cocos nucifera* | 0.5 |
| Perfume | 0.5 |
| Preservative(s) | 0.5 |

*Acacia honey, eucalyptus honey, pine honey and lavender honey in a ratio of 1:1:1.1:0.7

Phases A and B are produced separately by mixing at about 70° C. and are homogenized for about 20 minutes. After cooling to 35° C., phase C is added by stirring.

EXAMPLE 2

Lotion

| Phase A | |
|---|---|
| Water | q.s. ad 100 |
| Glycerol | 0.5 |
| Xanthan gum | 0.5 |
| Phase B | |
| Cyclopentasiloxane | 5.0 |
| Dicaprylyl carbonate | 5.0 |
| Phase C | |
| Honey complex* | 0.9 |
| Palm fruit milk of *Elaeis guinensis* | 1.0 |
| Palm leaf milk of *Phoenix canariensis* | 2.5 |
| Rice husk milk of *Oryza sativa* | 3.0 |
| Palm fruit milk of *Cocos nucifera* | 0.8 |
| Perfume | 0.5 |
| Preservative(s) | 0.5 |

*Acacia honey, eucalyptus honey, pine honey and lavender honey in a ratio of 1:1.2:0.9:0.7

The lotion is produced in the same way as in Example 1.

EXAMPLE 3

Night Cream

| Phase A | |
|---|---|
| PEG 20 methyl glucose sesquistearate 99.97%/Tocopherol 0.023% | 5.0 |
| Petroleum jelly | 2.0 |
| Shea butter | 1.0 |
| Phase B | |
| Water | q.s. ad 100 |
| Glycerol | 5.0 |
| Phase C | |
| Silicones | 6.0 |
| Phase D | |
| Honey complex* | 3.0 |
| Palm fruit milk of *Elaeis guinensis* | 1.0 |
| Palm leaf milk of *Phoenix canariensis* | 0.5 |
| Rice husk milk of *Oryza sativa* | 1.0 |
| Palm fruit milk of *Cocos nucifera* | 1.8 |
| Perfume | 0.5 |
| Preservative(s) | 0.5 |

*Acacia honey, eucalyptus honey, pine honey and lavender honey in a ratio of 1:1:0.8:0.8.

Phases A and B are produced separately by mixing at about 70° C. and are homogenized for about 20 minutes. After cooling to 50° C., phase C is added by stirring. After this, phase D is added to the mixture by stirring at about 35° C.

EXAMPLE 4

Comparative Tests

Skin moisture measurements were carried out with a corneometer on 20 female test subjects with dry combination skin. A corneometer CM 825 (Courage & Khazaka, Germany) was employed at 21° C. and 52% relative humidity.

The various creams were applied 2 hours after prior skin cleansing. The results of moisturizing in % are listed as mean values in the following table.

TABLE 1

| Time | Cream from Example 1 Without honey complex | Cream from Example 1 With honey complex | Cream from Example 1 EP 1185244 |
|---|---|---|---|
| 0.5 h | 35% | 63% | 94% |
| 2 h | 26% | 50% | 90% |
| 8 h | 15% | 31% | 88% |
| 24 h | 12% | 19% | 2% |

The comparison shows that the moisturizing effect of the cream from Example 1 of the present invention is significantly better with the honey complex than without this complex. Although the cream of EP 1185244 showed a higher moisture value after 8 hours than the present invention, it dropped after 24 h to almost zero while the inventive cream still showed moisture values of 20%.

The invention claimed is:

1. A moisture-regulating cosmetic composition comprising:
   (a) a watery plant milk of the fruit of *Elaeis guinensis*,
   (b) a watery plant milk of the leaves of *Phoenix canariensis*,
   (c) a watery plant milk of the rice husks of *Oryza sativa*,
   (d) a watery plant milk of the fruit of *Cocos nucifera*,
   (e) a honey complex consisting of acacia honey, eucalyptus honey, pine honey and lavender honey, and
   with cosmetic auxiliary substances and carrier substances as the remainder to make 100 wt. %, said percentages being based on the total weight of the cosmetic composition.

2. The cosmetic composition according to claim 1, wherein the plant milk of the fruit of *Elaeis guinensis* is 0.1 to 10 wt. % based on the total weight of the cosmetic composition.

3. The cosmetic composition according to claim 1, wherein the palm leaf milk of *Phoenix canariensis* is 0.1 to 5 wt. % based on the total weight of the cosmetic composition.

4. The cosmetic composition according to claim 1, wherein the rice husk milk of *Oryza sativa* is 0.1 to 5 wt. % based on the total weight of the cosmetic composition.

5. The cosmetic composition according to claim 1, wherein the watery plant milk of the fruit of *Cocos nucifera* is 0.1 to 7 wt. % based on the total weight of the cosmetic composition.

6. The cosmetic composition according to claim 1, wherein the honey complex of the cosmetic is 0.1 to 5 wt. % based on the total weight of the cosmetic composition.

7. A method of moisturizing of the skin comprising applying a cosmetic composition to the skin, said cosmetic composition comprising:
   0.1 to 10 wt. % by weight of a watery plant milk of the fruit of *Elaeis guinensis*,
   0.1 to 5 wt. % by weight of a watery plant milk of the leaves of *Phoenix canariensis*,
   0.1 to 5 wt. % by weight of a watery plant milk of the rice husks of *Oryza sativa*,
   0.1 to 7 wt. % by weight of a watery plant milk of the fruit of *Cocos nucifera*,
   0.1 to 5 wt. % of a honey complex consisting of acacia honey, eucalyptus honey, pine honey and lavender honey and
   cosmetic auxiliary substances and carrier substances to make 100 wt. %, said percentages being based on the total weight of the cosmetic composition.

8. A method of moisturizing the skin comprising applying to the skin a cosmetic composition comprising a watery plant milk of the fruit of *Elaeis guinensis*, a watery plant milk of the leaves of *Phoenix canariensis*, a watery plant milk of the rice husks of *Oryza sativa*, a watery plant milk of the fruit of *Cocos nucifera* and a honey complex consisting of acacia honey, eucalyptus honey, pine honey and lavender honey.

9. The cosmetic composition according to claim 2, comprising 0.5 to 5 wt. % of the plant milk of the fruit of *Elaeis guinensis* based on the total weight of the cosmetic composition.

10. The cosmetic composition according to claim 3, comprising 0.6 to 2 wt. % of the palm leaf milk of *Phoenix canariensis*, based on the total weight of the cosmetic composition.

11. The cosmetic composition according to claim 4, comprising 0.5 to 2.5 wt. % of the rice husk milk of *Oryza sativa*, based on the total weight of the cosmetic composition.

12. The cosmetic composition according to claim 5, comprising 0.2 to 3.0 wt. % of watery plant milk of the fruit of *Cocos nucifera*, based on the total weight of the cosmetic composition.

13. The cosmetic composition according to claim 6, comprising 0.1 to 2.5 wt. % of the honey complex based on the total weight of the cosmetic composition.

14. A moisture-regulating cosmetic composition comprising:

(a) a watery plant milk of the fruit of *Elaeis guinensis*,
(b) a watery plant milk of the leaves of *Phoenix canariensis*,
(c) a watery plant milk of the rice husks of *Oryza sativa*,
(d) a watery plant milk of the fruit of *Cocos nucifera*,
(e) a honey complex consisting of acacia honey, eucalyptus honey, pine honey and lavender honey, in the respective ratios of 1:0.5-1.4:0.4-1.3:0.6-1.8 and with cosmetic auxiliary substances and carrier substances as the remainder to make 100 wt. %, said percentages being based on the total weight of the cosmetic composition.

* * * * *

UNITED STATES PATENT AND TRADEMARK OFFICE
CERTIFICATE OF CORRECTION

| | | |
|---|---|---|
| PATENT NO. | : 7,906,158 B2 | |
| APPLICATION NO. | : 11/739294 | |
| DATED | : March 15, 2011 | |
| INVENTOR(S) | : Golz-Berner et al. | |

It is certified that error appears in the above-identified patent and that said Letters Patent is hereby corrected as shown below:

Column 6, line 38 reads "cosmetic auxiliary substances and carrier substances to" should read -- cosmetic auxiliary substances, carrier substances or other active substances to --

Signed and Sealed this
Fourth Day of September, 2012

David J. Kappos
*Director of the United States Patent and Trademark Office*